US006511463B1

(12) United States Patent
Wood et al.

(10) Patent No.: US 6,511,463 B1
(45) Date of Patent: Jan. 28, 2003

(54) METHODS OF FABRICATING MICRONEEDLE ARRAYS USING SACRIFICIAL MOLDS

(75) Inventors: Robert L. Wood, Cary, NC (US); Henry A. Wynands, Raleigh, NC (US); Karen W. Markus, Raleigh, NC (US)

(73) Assignee: JDS Uniphase Corporation, San Jose, CA (US)

( * ) Notice: Subject to any disclaimer, the term of this patent is extended or adjusted under 35 U.S.C. 154(b) by 0 days.

(21) Appl. No.: 09/442,827

(22) Filed: Nov. 18, 1999

(51) Int. Cl.⁷ ............................ A61M 5/00; H01R 43/04
(52) U.S. Cl. .................. 604/272; 29/884; 29/17.3; 604/191; 216/75
(58) Field of Search ............................ 604/272, 35, 43, 604/46, 501, 506, 181, 183, 186, 191, 239, 261; 29/890.01, 890.1, 884, 17.3, 17.1; 164/272, 421, 439; 264/219, 239, 323; 216/75, 100, 102

(56) References Cited

U.S. PATENT DOCUMENTS

| 3,964,482 A | 6/1976 | Gerstel et al. ............... 424/449 |
| 5,172,050 A | 12/1992 | Swapp .................... 324/158 P |
| 5,457,041 A | 10/1995 | Ginaven et al. .......... 435/172.1 |
| 5,476,211 A | 12/1995 | Khandros ................. 228/180.5 |
| 5,591,139 A | 1/1997 | Lin et al. .................... 604/264 |
| 5,658,515 A | 8/1997 | Lee et al. .................... 264/219 |
| 5,852,871 A | 12/1998 | Khandros ..................... 29/843 |
| 5,866,021 A | 2/1999 | Yagi et al. ..................... 216/84 |
| 5,869,974 A | 2/1999 | Akram et al. ................ 324/754 |
| 5,884,398 A | 3/1999 | Eldridge et al. .............. 29/843 |
| 5,928,207 A | 7/1999 | Pisano et al. ................. 604/272 |
| 6,334,856 B1 * | 1/2002 | Allen et al. ................. 604/191 |

OTHER PUBLICATIONS

Brazzle et al., *Fluid–Coupled Hollow Metallic Microfabricated Needle Arrays,* SPIE Conference on Microfluidic Devices and Systems, vol. 2515, Sep. 1998, pp. 116–124.

Talbot et al., *Polymolding: Two Wafer Polysilicon Micromolding of Closed–Flow Passages for Microneedles and Microfluidic Devices,* Solid–State Sensor and Actuator Workshop, 1998, pp. 265, 268.

International Search Report, PCT/CA 00/01210, Jan. 23, 2001.

Papautsky et al., *Micromachined Pipette Arrays (MPA),* Proceedings—19th International Conference—IEEE/EMBS, Oct. 30–Nov. 2, 1997, Chicago, IL, pp. 2281–2284.

* cited by examiner

*Primary Examiner*—Anhtuan T. Nguyen
(74) *Attorney, Agent, or Firm*—Myers Bigel Sibley & Sajovec

(57) ABSTRACT

Microneedle arrays are fabricated by providing a sacrificial mold including a substrate and an array of posts, preferably solid posts, projecting therefrom. A first material is coated on the sacrificial mold including on the substrate and on the array of posts. The sacrificial mold is removed to provide an array of hollow tubes projecting from a base. The inner and outer surfaces of the array of hollow tubes are coated with a second material to create the array of microneedles projecting from the base. The sacrificial mold may be fabricated by fabricating a master mold, including an array of channels that extend into the master mold from a face thereof. A third material is molded into the channels and on the face of the master mold, to create the sacrificial mold. The sacrificial mold then is separated from the master mold. Alternatively, wire bonding may be used to wire bond an array of wires to a substrate to create the sacrificial mold. The first material preferably is coated on the sacrificial mold by plating. Prior to plating, a plating base preferably is formed on the sacrificial mold including on the substrate and on the array of posts. The inner and outer surfaces of the array of hollow tubes preferably are coated with the second material by overplating the second material on the inner and outer surfaces of the array of hollow tubes.

23 Claims, 5 Drawing Sheets

METHODS OF FABRICATING MICRONEEDLE ARRAYS USING SACRIFICIAL MOLDS

FIELD OF THE INVENTION

This invention relates to hypodermic needles, and more particularly to microneedles and fabrication methods thereof.

BACKGROUND OF THE INVENTION

Hypodermic needles are widely used in the biomedical field for injection into and extraction from living tissue. Hypodermic needles generally have a relatively large diameter, for example on the order of millimeters. Unfortunately, the large diameter can damage biological tissue during penetration. Moreover, tissue penetration often is painful due to the relatively large needle diameter.

Accordingly, microneedles are being developed, that can have diameters that are on the order of microns. The smaller diameter needle can reduce damage to living tissue and/or reduce pain. More precise injection and extraction also may be provided. In order to inject or extract a requisite amount of liquid through a microneedle of relatively small diameter, an array of microneedles, often referred to as a microneedle array, generally is provided. For example, a microneedle array may have dimensions on the order of 1 cm$^2$ and may include tens, hundreds or even thousands of microneedles thereon. Microneedles are described in U.S. Pat. No. 5,457,041 to Ginaven et al. entitled Needle Array and Method of Introducing Biological Substances Into Living Cells Using the Needle Array; U.S. Pat. No. 5,658,515 to Lee et al. entitled Polymer Micromold and Fabrication Process; U.S. Pat. No. 5,591,139 to Lin et al. entitled IC-Processed Microneedles; and U.S. Pat. No. 5,928,207 to Pisano et al. entitled Microneedle With Isotropically Etched Tip, and Method of Fabricating Such a Device.

Microneedles may be fabricated using micromachining or other processes that are used to form microelectromechanical systems (MEMS). These fabrication steps may be similar to those that are used for fabricating integrated circuit microelectronic devices and thereby may be capable of relatively low-cost fabrication in large numbers. Unfortunately, notwithstanding the applicability of microelectronic fabrication techniques to the fabrication of microneedle arrays, there continues to be a need to provide improved fabrication processes for microneedle arrays that can produce microneedle arrays at very low cost, for example, less than one dollar per microneedle array and preferably less than one cent per microneedle array.

SUMMARY OF THE INVENTION

The present invention provides methods of fabricating microneedle arrays by providing a sacrificial mold including a substrate and an array of posts, preferably solid posts, projecting therefrom. A first material is coated on the sacrificial mold including on the substrate and on the array of posts. The sacrificial mold is removed to provide an array of hollow tubes projecting from a base. The outer surfaces, and preferably the inner surfaces, of the array of hollow tubes are coated with a second material to create the array of microneedles projecting from the base. By using a sacrificial molding technique, low cost fabrication of microneedles may be obtained. Moreover, the sacrificial mold may be fabricated from plastic and/or metal, and need not be fabricated from a relatively expensive silicon semiconductor wafer. Low cost microneedle arrays thereby may be provided.

The sacrificial mold may be fabricated by fabricating a master mold, including an array of channels that extend into the master mold from a face thereof. A third material is molded into the channels and on the face of the master mold, to create the sacrificial mold. The sacrificial mold then is separated from the master mold. Alternatively, wire bonding that is widely used in the fabrication of microelectronic devices, may be used to wire bond an array of wires to a substrate to create the sacrificial mold.

The first material preferably is coated on the sacrificial mold by plating. When the sacrificial mold is not conductive, a plating base preferably is formed on the sacrificial mold including on the substrate and on the array of posts prior to plating. The inner and outer surfaces of the array of hollow tubes preferably are coated with a second material by overplating the second material on the inner and outer surfaces of the array of hollow tubes. The plating base preferably comprises at least one of copper and gold, including alloys thereof. The first material preferably comprises at least one of nickel and chromium, including alloys thereof. The second material preferably comprises at least one of gold, rhodium, platinum and ruthenium, including alloys thereof.

When coating the first material on the sacrificial mold including on the substrate and on the array of posts, the tips of the array of posts preferably are left uncoated so that open tubes later result. Alternatively, the tips may be removed to provide the array of hollow tubes. Moreover, the tips of the array of hollow tubes may be sharpened, for example by etching the tips. The first material may be coated on the array of posts including an obliquely extending portion of the tips. Thus, an obliquely angled tip may be formed which can increase the ability to penetrate living tissue without clogging.

First and second preferred embodiments for fabricating microneedle arrays according to the present invention now will be described. The first embodiment uses a soluble mold, whereas the second embodiment uses an array of wires projecting from a substrate.

In particular, according to the first preferred embodiments, a soluble mold is provided including a substrate and an array of posts, preferably solid posts, projecting therefrom. A plating base is formed on the soluble mold including on the substrate and on the array of posts. A plated first material is formed on the plating base except for across the tips of the array of posts. The soluble mold then is at least partially dissolved and thereby removed, to provide an array of hollow tubes projecting from a base. In order to provide the array of hollow tubes, the tips of the tubes may be removed in a separate operation. The plating base preferably also is at least partially dissolved and removed along with the soluble mold. The inner and outer surfaces of the array of hollow tubes preferably are overplated with a second material, to create the array of microneedles projecting from the base. The tips of the array of hollow tubes may be sharpened, preferably by etching the tips.

The soluble mold preferably is fabricated by fabricating the master mold including an array of channels that extend into the master mold from a face thereof. A soluble material then is molded into the channels and on the face of the master mold, to create the soluble mold. Conventional molding processes, such as injection molding, embossing, casting and/or sheet forming may be used. The soluble mold then is separated from the master mold.

When plating and/or overplating the microneedle array, the tips of the array preferably are masked to prevent plating of the tips across the entrance of the tube. Masking may be accomplished by masking the tips of the soluble mold to prevent formation of the plating base on the tips. Alternatively, the tips of the plating base may be masked to prevent further plating thereon. When masking, the tips preferably are masked at an oblique angle, to thereby allow plating of an obliquely extending portion of the tips, and thereby create angled needle points that can have reduced susceptibility to clogging.

In second preferred embodiments of the invention, a sacrificial mold is provided including a substrate and an array of wires projecting therefrom. A plated first material is formed on the sacrificial mold including on the substrate and on the array of wires except for across the tips of the wires. The sacrificial mold is removed to provide an array of hollow tubes projecting from a base. In order to provide the array of hollow tubes, the tips of the tubes may be removed in a separate operation. The inner and outer surfaces of the array of hollow tubes are overplated with a second material, to create the array of microneedles projecting from the base. In a preferred embodiment, the steps of wire bonding, plating, removing and overplating are performed in a continuous process followed by singulating individual arrays of microneedles.

The sacrificial mold preferably is provided by wire bonding an array of wires to a substrate to create the sacrificial mold. Wire bonding may be performed by wire bonding both ends of a plurality of wires to the substrate, to create a plurality of loops of wires on the substrate. The loops of wires then may be cut, or the centers of the loops may be masked to prevent plating, to create the sacrificial mold. Sharpening and oblique angle tip masking also preferably are performed, as was described above.

Microneedle arrays according to the present invention preferably comprise a monolithic core including a substrate having an array of holes therein and an array of hollow tubes that project from the substrate, a respective one of which surrounds a respective one of the array of holes. An overlayer also is provided on the monolithic core, on the outer surfaces of the array of hollow tubes, on the tips of the array of hollow tubes, and preferably on the inner surfaces of the array of hollow tubes.

The monolithic core also may comprise an array of shoulders that surround the array of hollow tubes adjacent the substrate. The shoulders may arise from the wire bonding region between the wires and the substrate of the sacrificial mold. The array of hollow tubes also may have scalloped outer surfaces. The scalloped outer surfaces may be caused by deep reactive ion etching which may be used to form the master mold.

The array of hollow tubes preferably includes sharp ends that more preferably extend at an oblique angle relative to the substrate. The monolithic core preferably comprises at least one of nickel and chromium including alloys thereof, most preferably nickel including alloys thereof. The overlayer preferably comprises at least one of gold, rhodium, platinum and ruthenium, and alloys thereof, and most preferably gold or alloys thereof. Microneedle arrays may be provided thereby.

BRIEF DESCRIPTION OF THE DRAWINGS

FIGS. 1A', 1C' and 1D'–1D''' are enlarged cross-sectional views showing alternate fabrication steps for FIGS. 1A, 1C and 1D respectively.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout. It will be understood that when an element such as a layer, region or substrate is referred to as being "on" another element, it can be directly on the other element or intervening elements may also be present. In contrast, when an element is referred to as being "directly on" another element, there are no intervening elements present.

Figure 1A:
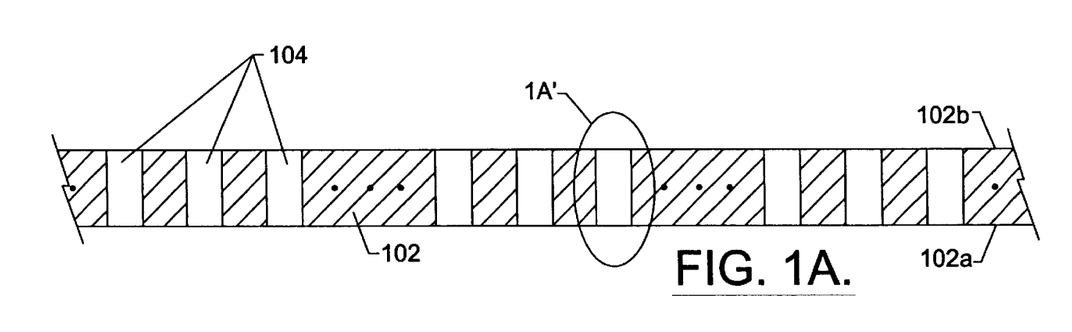
FIGS. 1A–1F are cross-sectional views of microneedle arrays during intermediate fabrication steps, according to the present invention.
Figure 1B:
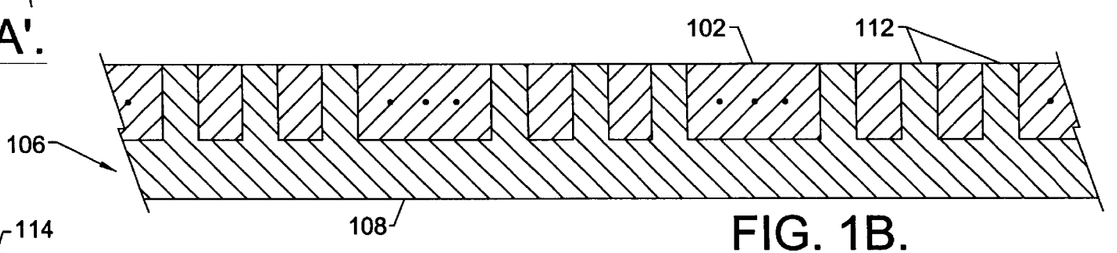
Figure 1C:
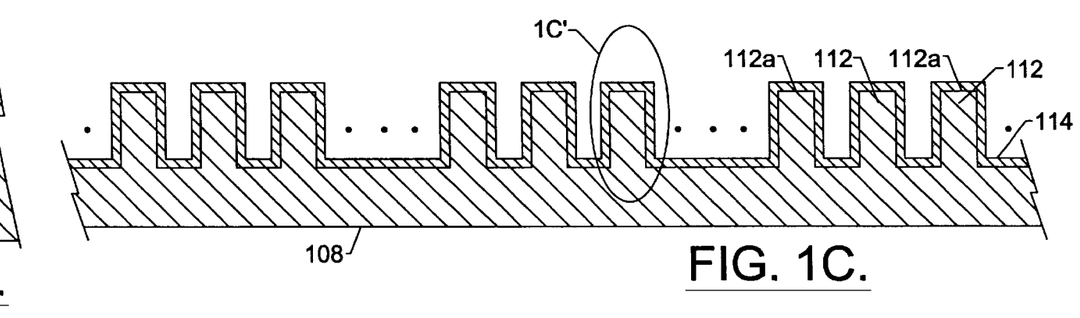
Figure 1D:
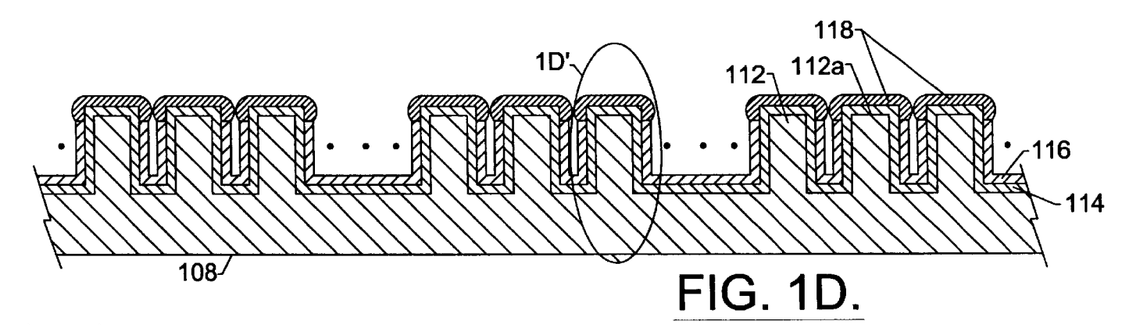
Figure 1E:
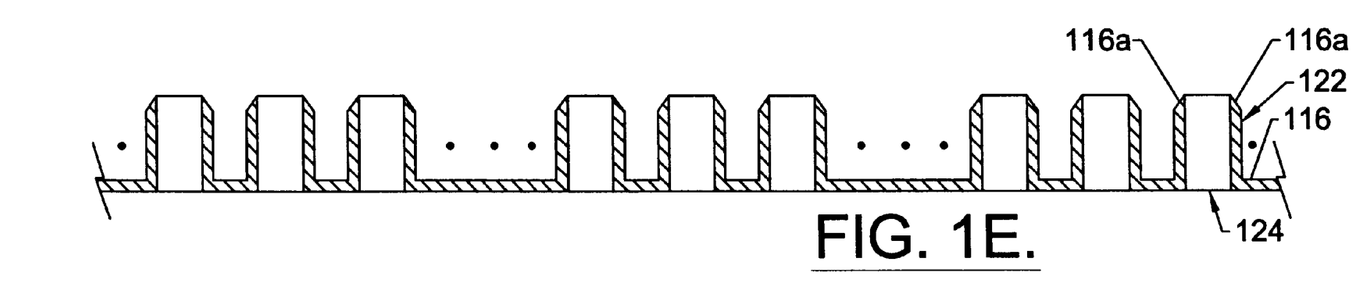
Figure 1F:
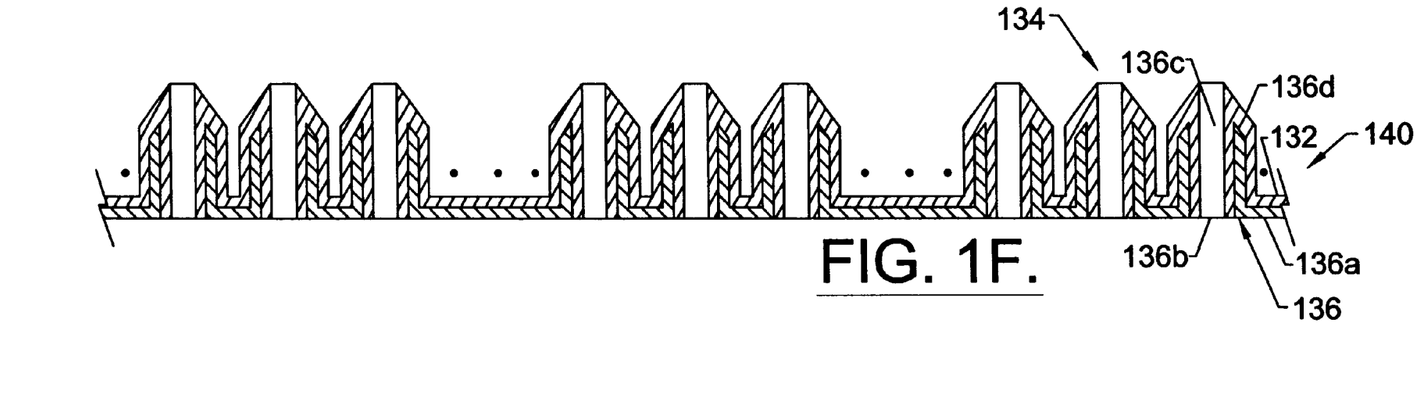

FIGS. 1A 1F are cross-sectional views of microneedle arrays during intermediate fabrication steps, according to the present invention.

Referring now to FIG. 1A, a master mold 102 is fabricated. The master mold may comprise silicon, metal and/or other mold materials. The master mold 102 includes an array of channels 104 therein that extend into the master mold from a first face 102$a$ thereof. As shown in FIG. 1A, the channels also may extend through the master mold 102 to a second face 102$b$ thereof. However, the channels need not extend entirely through the master mold. The master mold may be between about 50 $\mu$m and about 1 mm in thickness, and the channels may be between about 10 $\mu$m and about 100 $\mu$m in diameter. The channels may be formed in the master mold using deep Reactive Ion Etching (RIE) in a silicon or other master mold and/or using the LIGA process in a metal mold, preferably nickel. Deep RIE and the LIGA process are well known to those having skill in the art, and are described, for example, in the assignee's web site www.memsrus.com.

It will be understood by those having skill in the art that although only nine channels 104 are illustrated in FIG. 1A, fewer or more channels may be provided depending upon the desired number of microneedles. In fact, only a single channel may be included in the array 104. A conventional microneedle array may have dimensions on the order of 1 cm$^2$, similar to a conventional integrated circuit chip, and may contain tens, hundreds or thousands of needles. However, a single needle also may be provided. The needles may be equally spaced or unequally spaced. It also will be understood that a single master mold may be used to fabricate a plurality of microneedle arrays which then are diced into individual microneedle arrays after processing. Thus, the master mold 102 may have an area on the order of 1 cm$^2$ but may be 1000 cm$^2$ or larger in area. When forming the channels using deep RIE, the channels may have scalloped walls, as shown in the enlarged view of FIG. 1A'. These scalloped walls may replicate during subsequent steps, as will be described below. When LIGA or other processes are used to form the channels, smooth channels as shown in FIG. 1A may be present, and may replicate during subsequent steps.

Referring now to FIG. 1B, a soluble material, such as a soluble polymer, including Poly Methyl Methacrylate (PMMA) or poly-carbonate, is molded into the channels 104 and on the face 102a of the master mold 102 to create a soluble mold 106. As shown in FIG. 1B, the soluble mold includes a substrate 108 and an array of posts 112, preferably solid posts, projecting therefrom. The soluble mold may be created using conventional microinjection molding. Since the soluble mold will be at least partially dissolved later in the process, as described below, a material that can be at least partially dissolvable preferably is used. It will be understood that conventional molding techniques may be used, including injection molding, embossing, casting and/or sheet forming.

Then, referring to FIG. 1C, a plating base 114 is formed on the soluble mold including on the substrate 108 and on the array of posts 112. The plating base 114 may be formed by conventional sputtering or other conventional techniques. The plating base may comprise copper, gold and/or alloys thereof, more preferably copper and/or alloys thereof. The thickness of the plating base may be about 1000 Å.

Still referring to FIG. 1C, it can be seen that the plating base covers the array of solid posts 112 including across the tips 112a thereof. Since it is desirable to eventually form hollow microneedles with open tips, the plating base may be prevented from depositing on the tips 112a of the posts 112 by masking the tips 112a. Alternatively, after deposition of the plating base, the tips 112a may be dipped into an etchant to remove the plating base 114 from on the tips 112a, as shown in FIG. 1C'. In yet another alternative that will be described in connection with FIG. 1D, the plating base 114 is allowed to remain across the tips 112a of the solid posts 112, but a subsequent plated layer is masked from the tips or is subsequently removed.

Referring now to FIG. 1D, a plated first material 116 is formed on the plating base. The first material preferably comprises nickel, chromium and/or alloys thereof, more preferably nickel and/or alloys thereof, and may have a thickness between about 10 $\mu$m and about 20 $\mu$m. Multiple sublayers of first materials also may be formed.

As shown in FIG. 1D, prior to plating the first material 116, a mask 118 may be formed on the tips 112a to prevent plating across the tips 112a. In another alternative, the first material 116 may be plated across the tips 112a and then the first material and optionally the plating base across the tips 112a may be removed, for example by dipping into a chemical etch. The ends of the posts 112 also may be removed. In yet another alternative, the first material 116, and optionally the plating base across the tips 112a may be removed using mechanical abrasion or other known techniques. In order to ensure that the posts 112 do not break during mechanical abrasion, the structure may first be encapsulated, for example in a spun-on polymer, the tips may be abraded and the spun-on polymer may be removed. In any of these alternative operations, the height of the hollow tubes also may be reduced as desired. Accordingly, the step of forming a plated first material on the plating base except for across the tips of the array of posts, according to the present invention, contemplates masking the tips so that the first material is not plated on the tips or plating the first material on the tips and then removing this material, using any of the above-disclosed or other techniques.

Referring now to FIG. 1E, the mask 118 may be removed, if present, and the tips 116a of the first material 116 may be sharpened, for example using mechanical and/or chemical etching. Sharpening may improve the puncturing ability of the microneedle array. Then, the soluble mold 106 is released, preferably by at least partially dissolving the soluble mold. For example, when the soluble mold comprises PMMA, it may be dissolved in acetone. The plating base 114 also preferably is dissolved to provide an array of hollow tubes 122 projecting from a base 124.

Then, referring to FIG. 1F, the outer surfaces, and preferably the inner surfaces, of the array of hollow tubes 122 are overplated with a second material 132, to create an array of microneedles 134 projecting from a base 136. As shown in FIG. 1F, the base of the first layer 124 also preferably is overplated with the second material. Both faces of the base also may be overplated. The second material preferably comprises a biocompatible material such as gold, rhodium, platinum, ruthenium and/or alloys thereof, and preferably gold. The thickness of the second material preferably is between about 0.5 $\mu$m and about 10 $\mu$m. Multiple sublayers of the second materials also may be formed. Since the inside and outside surfaces of the microneedles 134 are overplated, a biocompatible microneedle may be provided.

FIGS. 1D'–1D'" are enlarged views of the indicated portion of the FIG. 1D, and illustrate another aspect of the present invention. As is well known to those having skill in the art, it is desirable for a needle to have a slanted or oblique tip to allow improved penetration and reduced clogging. In order to form a slanted or oblique tip, the mask 118 may be formed asymmetrically on the tips 112a. For example, as shown in FIG. 1D, the mask 118 may be a photoresist. The photoresist is baked to dry the photoresist. The photoresist then is exposed to radiation 138 at an oblique angle. The photoresist then is developed to produce the-asymmetrical mask 118'. Plating of the first material 116 then is performed to form a layer of the first material 116' on the plating base 114 that is asymmetrical and provides a slanted tip. In other alternatives, the masking material may be deposited at an oblique angle or other techniques may be used to asymmetrically form the mask on the tips. The asymmetrical mask may be formed directly on the plating base or the first material. In yet another alternative, asymmetrical etching techniques may be used to asymmetrically etch the tips to provide slanted tips.

Referring again to FIG. 1F, a microneedle array 140 according to the present invention includes a monolithic core 136 including a substrate 136a having an array of holes 136b therein, and an array of hollow tubes 136c that project from the substrate 136a, a respective one of which surrounds a respective one of the array of holes 136b. An overlayer 132 also is provided, that extends on the substrate 136a, on the outer surfaces of the array of hollow tubes 136c, on the tips 136d of the hollow tubes and preferably on the inner surfaces of the array of hollow tubes 136c. The overlayer also may extend on the back face of the substrate 136a. The hollow tubes may have scalloped outer surfaces reflecting the scallops shown in FIG. 1A', due to the scalloped surfaces of the channels 104. The hollow tubes preferably include sharp ends as shown in FIG. 1F, and the ends of the arrays of hollow tubes preferably extend at an oblique angle relative to the substrate as shown in FIG. 1D". The monolithic core preferably comprises at least one of nickel and chromium, including alloys thereof, and the overlayer preferably comprises at least one of gold, rhodium, platinum and ruthenium and alloys thereof. More preferably, the monolithic core comprises nickel or alloys thereof and the overlayer more preferably comprises gold or alloys thereof. The monolithic core and/or the overlayer may comprise multiple sublayers.

FIGS. 2A–2E are cross-sectional views of microneedle arrays during intermediate fabrication steps, according to the present invention. In general, FIGS. 2A–2E wire bond an array of wires to a substrate to create a sacrificial mold, rather than molding from a master mold, as was the case in FIGS. 1A–1B. The other processing steps may be similar to FIGS. 1C–1F, as will be described below. Moreover, the optional steps of FIGS. 1C'–1D" also may be applied, as will be described below.

Figure 2A:
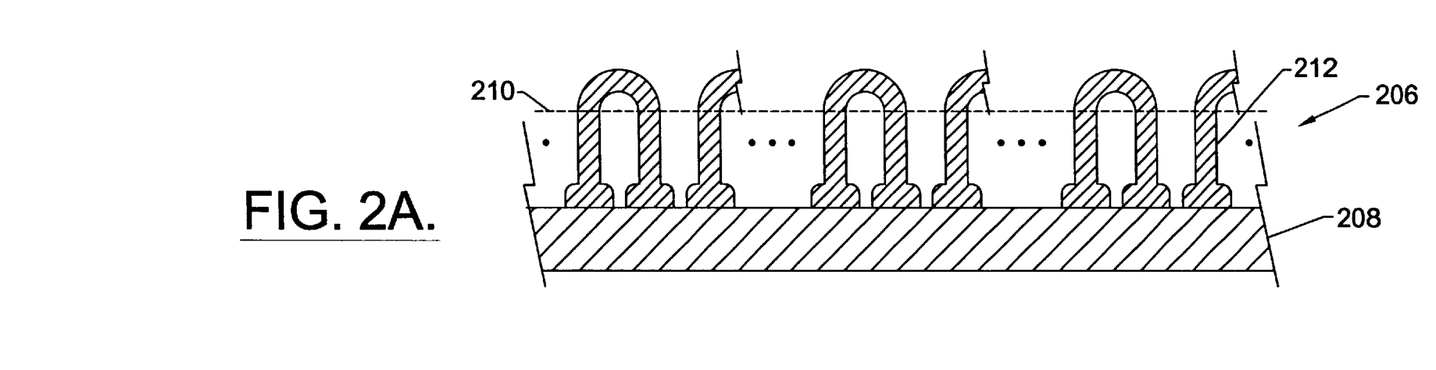
FIGS. 2A–2E are cross-sectional views of other microneedle arrays during intermediate fabrication steps according to the present invention.

More specifically, referring to FIG. 2A, a sacrificial mold 206 is fabricated by wire bonding a plurality of wires 212 to a substrate 208. Wire bonding is a technique that is well known to those having skill in the microelectronic fabrication art, and is described, for example, in U.S. Pat. No. 5,476,211 to Khandros entitled Method of manufacturing Electrical Contacts, Using a Sacrificial Member; U.S. Pat. No. 5,852,871 to Khandros entitled Method of Making Raised Contacts on Electronic Components; and U.S. Pat. No. 5,884,398 to Eldridge et al. entitled Mounting Spring Elements on Semiconductor Devices. The substrate 208 may be a discrete substrate that is large enough for one or more microneedle arrays. Alternatively, and preferably, the substrate 208 is a continuous substrate and wires 212 are wire-bonded to the substrate 208 in a continuous wire bonding process.

Figures 2B, 2C:
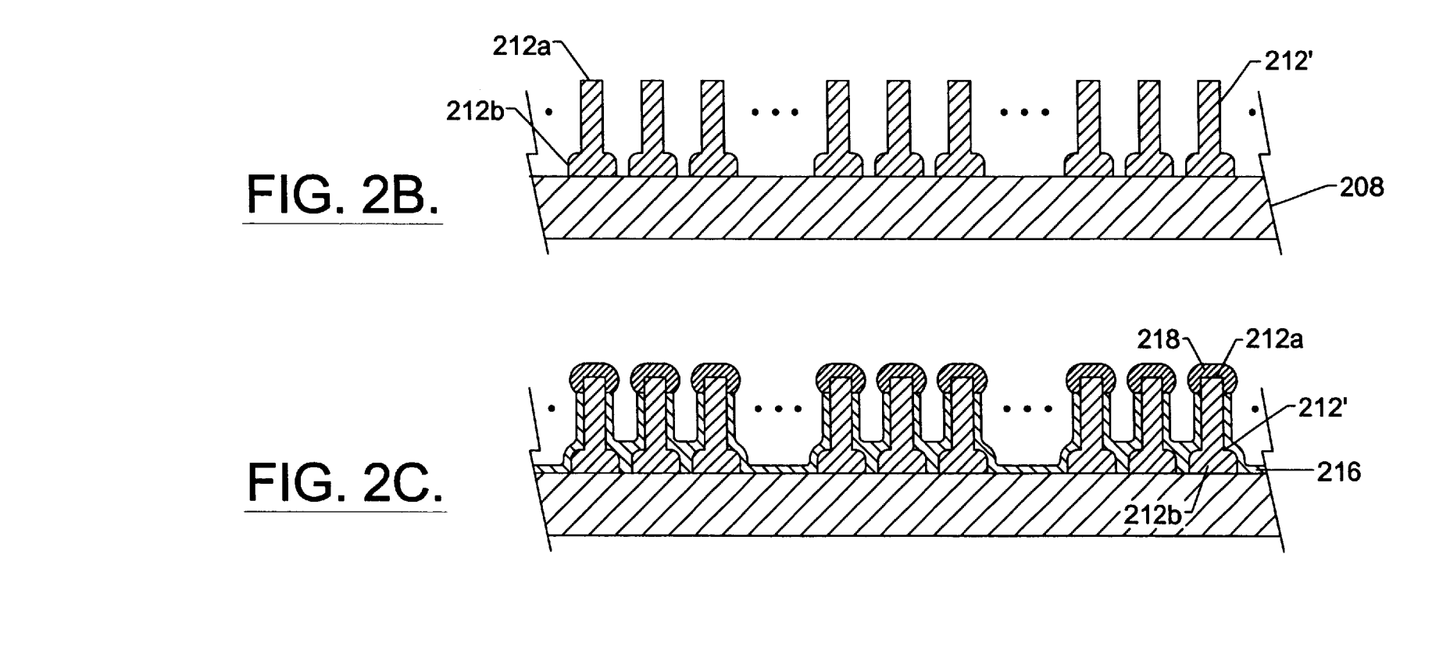

As shown in FIG. 2A, both ends of a plurality of wires 212 are bonded to the substrate 208 to create a plurality of loops of wires on the substrate 208. Then, as shown in FIG. 2A, the wires may be cut, for example along a line 210 that extends parallel to the substrate 208, to provide an array of wires 212' that project from the substrate 208. Alternatively, one end of a plurality of wires may be wire-bonded to the substrate 208 to produce the structure of FIG. 2B, without first forming the loops of FIG. 2A and then cutting along the line 210. As shown in FIG. 2B, each wire 212' includes a tip 212a and a shoulder 212b that is characteristic of wire bonding. The substrate 208 preferably comprises copper or alloys thereof and the wires 212' also preferably comprise copper or alloys thereof.

Referring now to FIG. 2C, a plated first material 216 is formed on the sacrificial mold 206 including on the substrate and on the array of wires 212', except for across the tips 212a of the wires 212'. The first material may be similar to the first material 116 of FIG. 1A. As was already described in connection with FIGS. 1A–1F, many alternatives may be provided so as not to block the tips 212a of the wires 212'. In one example, shown in FIG. 2C, a mask 218 is formed on the tips 212a. The mask may be formed in the same manner as mask 118 of FIG. 1D, and may be asymmetrically formed as was shown in FIGS. 1D'–1D'''.

Figure 2D:
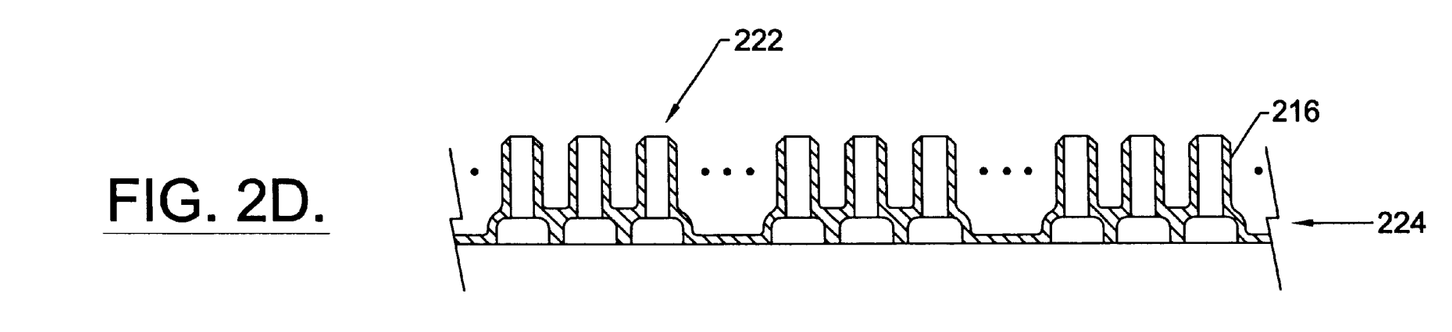

Then, referring to FIG. 2D, the sacrificial mold 206 is removed to provide an array of hollow tubes 222 projecting from a base 224. The tips of the tubes may be sharpened, as was described in connection with FIG. 1E. The tips may be removed to open the hollow tubes as was described above.

Figure 2E:
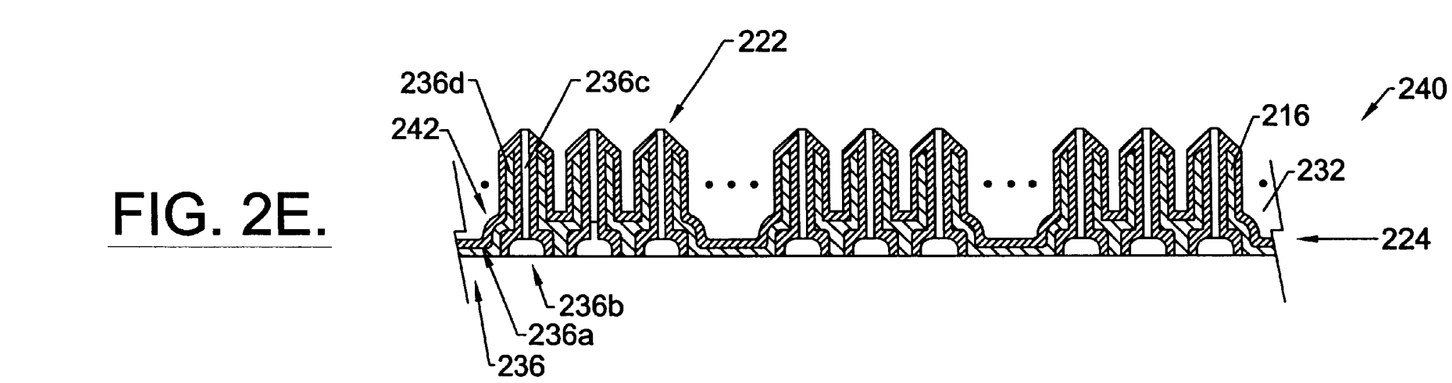

Then, referring to FIG. 2E, the outer surfaces, and preferably the inner surfaces, of the array of hollow tubes 222, and preferably the base 224, and optionally the back face of the base 224 are overplated with a second material 232, to create the array of microneedles projecting from the base 224. The second material may comprise the same materials as the second material 132 of FIG. 1F. The microneedle arrays then may be singulated from the continuous structure of FIG. 2E.

The fabrication methods of FIGS. 2A–2E can eliminate the need to perform micromolding and can utilize well known wire bonding techniques. However, since the wires generally are bonded individually rather than molded as a unit, this fabrication process may be more costly.

Microneedle arrays 240 that are fabricated according to methods of FIGS. 2A–2E include a monolithic core 236 including the substrate 236a having an array of holes 236b therein and an array of hollow tubes 236c that project from the substrate 236, a respective one of which surrounds a respective one of the array of holes 236b. An overlayer 232 is provided on the monolithic substrate core 236, on the outer surfaces of the array of hollow tubes 236c, on the tips 236d of the array of hollow tubes and preferably on the inner surfaces of the array of hollow tubes. Due to the wire bonding process, an array of shoulders 242 also is provided that surrounds the array of hollow tubes 236c adjacent the substrate 236. As was already described, the array of hollow tubes may include sharp ends and/or may extend at an oblique angle relative to the substrate.

Accordingly, microneedle arrays need not use silicon semiconductor substrates and/or silicon micromachining techniques, both of which may be costly and/or complex. Rather, they can use metal and/or plastic substrates, as was described above. Accordingly, low cost microneedle arrays and/or simplified fabrication methods therefor may be provided.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of fabricating a microneedle array comprising the steps of:

providing a soluble mold including a substrate and an array of posts projecting therefrom;

forming a plating base on the soluble mold including on the substrate and on the array of posts;

forming a plated first material on the plating base except for across the tips of the array of posts;

at least partially dissolving the soluble mold to provide an array of hollow tubes projecting from a base; and overplating the outer surfaces of the array of hollow tubes with a second material to create the array of microneedles projecting from the base.

2. A method according to claim 1 wherein the step of providing a soluble mold comprises the steps of:

fabricating a master mold including an array of channels that extend into the master mold from a face thereof;

molding a soluble material into the channels and on the face of the master mold to create the soluble mold; and separating the soluble mold from the master mold.

3. A method according to claim 1 further comprising the step of:

sharpening the tips of the array of hollow tubes.

4. A method according to claim 3 wherein the step of sharpening comprises the step of etching the tips of the array of hollow tubes.

5. A method according to claim 1 wherein the at least partially dissolving step comprises the step of at least partially dissolving the soluble mold and the plating base to provide an array of hollow tubes projecting from a base.

6. A method according to claim 1 wherein the step of forming a plated first material is preceded by the step of masking the tips of the array of posts to prevent plating of the tips.

7. A method according to claim 1 wherein the step of forming a plating base is preceded by the step of masking the tips of the soluble mold to prevent formation of the plating base on the tips.

8. A method according to claim 6 wherein the step of masking the tips comprises the step of masking the tips of the array of posts at an oblique angle thereto to prevent plating of an obliquely extending portion of the tips.

9. A method according to claim 7 wherein the step of masking the tips comprises the step of masking the tips of the soluble mold at an oblique angle thereto to prevent formation of the plating base on an obliquely extending portion of the tips.

10. A method according to claim 7 wherein the plating base comprises at least one of copper and gold, wherein the first material comprises at least one of nickel and chromium and wherein the second material comprises at least one of gold, rhodium, platinum and ruthenium.

11. A method according to claim 1 wherein the following step is performed between the steps of at least partially dissolving and overplating:

removing the tips of the hollow tubes to reduce the height of the hollow tubes.

12. A method according to claim 1 wherein the step of overplating comprises the step of:

overplating the inner and outer surfaces of the array of hollow tubes with the second material to create the array of microneedles projecting from the base.

13. A method of fabricating a microneedle array comprising the steps of:

providing a sacrificial mold including a substrate and an array of wires projecting therefrom;

forming a plated first material on the sacrificial mold including on the substrate and on the array of wires except for across the tips of the wires;

removing the sacrificial mold to provide an array of hollow tubes projecting from a base; and overplating the outer surfaces of the array of hollow tubes with a second material to create the array of microneedles projecting from the base.

14. A method according to claim 13 wherein the step of providing a sacrificial mold comprises the step of wire bonding an array of wires to a substrate to create the sacrificial mold.

15. A method according to claim 14 wherein the steps of wire bonding, plating, removing and overplating are performed in a continuous process and wherein the step of overplating is followed by the step of singulating individual arrays of microneedles.

16. A method according to claim 14 wherein the step of wire bonding comprises the steps of:

wire bonding both ends of a plurality of wires to the substrate to create a plurality of loops of wires on the substrate; and cutting the loops of wires to create the sacrificial mold.

17. A method according to claim 13 further comprising the step of:

sharpening the tips of the array of hollow tubes.

18. A method according to claim 17 wherein the step of sharpening comprises the step of etching the tips of the array of hollow tubes.

19. A method according to claim 13 wherein the step of forming a plated first material is preceded by the step of masking the tips of the array of wires to prevent plating of the tips.

20. A method according to claim 19 wherein the step of masking the tips comprises the step of masking the tips of the array of wires at an oblique angle to prevent plating of an obliquely extending portion of the tips.

21. A method according to claim 13 wherein the wires comprise at least one of copper and gold, wherein the first material comprises at least one of nickel and chromium and wherein the second material comprises at least one of gold, rhodium, platinum and ruthenium.

22. A method according to claim 13, wherein the following step is performed between the steps of removing and overplating:

removing the tips of the hollow tubes to reduce the height of the hollow tubes.

23. A method according to claim 13 wherein the step of overplating comprises the step of:

overplating the inner and outer surface of the array of hollow tubes with the second material to create the array of microneedles projecting from the base.

* * * * *